United States Patent [19]

Chao et al.

[11] 4,366,332
[45] Dec. 28, 1982

[54] CATALYTIC HYDROGENOLYSIS OF ALDITOLS TO PRODUCT GLYCEROL AND POLYOLS

[75] Inventors: James C. Chao, West Nyack, N.Y.; Derk T. A. Huibers, Pennington, N.J.

[73] Assignee: Hydrocarbon Research, Inc., Lawrenceville, N.J.

[21] Appl. No.: 227,036

[22] Filed: Jan. 21, 1981

[51] Int. Cl.³ .................. C07C 31/22; C07C 31/20; C07C 31/24; C07C 31/26
[52] U.S. Cl. .................................................. 568/863
[58] Field of Search ........................... 568/861, 863

[56] References Cited

U.S. PATENT DOCUMENTS

| | | | |
|---|---|---|---|
| 2,004,135 | 6/1935 | Rothrock | 568/861 |
| 2,174,651 | 10/1939 | Byrkit | 568/863 |
| 2,456,633 | 12/1948 | Haensel | 252/460 |
| 2,549,416 | 4/1951 | Brooks | 568/881 |
| 2,851,390 | 12/1957 | Gwynn et al. | 568/882 |
| 2,852,570 | 9/1958 | Conradin et al. | 568/861 |
| 2,965,679 | 12/1960 | Conradin et al. | 568/861 |
| 3,481,836 | 12/1969 | Nomura et al. | 568/863 |
| 3,676,364 | 7/1972 | Coates | 568/861 |

FOREIGN PATENT DOCUMENTS

| | | | |
|---|---|---|---|
| 523789 | 4/1956 | Canada | 568/863 |
| 35860 | 1/1965 | Fed. Rep. of Germany | 568/863 |
| 688515 | 3/1953 | United Kingdom | 568/863 |

OTHER PUBLICATIONS

Lang "Handbook of Chemistry", 10th ed. (1961), pp. 951, 952.

*Primary Examiner*—Joseph E. Evans
*Attorney, Agent, or Firm*—Vincent A. Mallare; Fred A. Wilson

[57] ABSTRACT

Alditols such as 15–40 W. % sorbitol solution in water are catalytically hydrocracked in a fixed bed reaction process using a high activity nickel catalyst to produce at least about 30 W. % conversion to glycerol and glycol products. The feedstream pH is controlled to prevent catalyst damage by adding a basic promotor material such as calcium hydroxide. Reaction zone conditions are maintained at 420°–520° F. temperature, 1200–2000 psig hydrogen partial pressure, and liquid hourly space velocity of 1.5 to 3.0. To maintain desired activity and glycerol yield, the catalyst is regenerated to provide catalyst age of 8–200 hours. The reaction products are separated in a recovery step, and any alditols can be recycled to the reaction zone for further hydrogenolysis to produce 40–90 W. % glycerol product. Sorbitol conversion is maintained preferably at between about 30–70 W. % by catalyst regeneration following 10 to 50 hours use, comprising washing with solvent to remove deposits and by heating the catalyst with reducing gas at 500°–600° F. temperature and at reduced pressure to remove surface oxidation.

12 Claims, 6 Drawing Figures

CATALYTIC HYDROGENOLYSIS OF ALDITOLS TO PRODUCT GLYCEROL AND POLYOLS

BACKGROUND OF INVENTION

This invention pertains to the hydrogenolysis of alditols such as sorbitol to produce glycerol and glycol products using a continuous fixed bed catalytic process.

The production of glycerol and polyols by hydrogenolysis of sorbitol has been widely studied. Generally, an optimum 30–40 W % of glycerol congeners has been reported in the product obtained from autoclave batch reaction processes. The reaction conditions used are high hydrogen partial pressure of 2000–5000 psig, temperature of 200°–250° C., (392°–482° F.), long residence time of 1.5 hours or more, and use of fine nickel powder catalyst of 100–200 mesh size in the form of a slurry with the feed.

A disclosure regarding hydrogenolysis of sorbitol is provided by Clark in Industrial & Engineering Chemistry, Vol. 50, No. 8 (August 1958), page 1125. Aqueous solution containing 40% of 99% D-sorbitol were used with 1% calcium hydroxide promotor and 50% nickel on kieselguhr catalyst suspended in a slurry with the feed in a stirred reactor. Conditions used were 2000–5600 psi hydrogen partial pressure, 215°–245° C. (419°–473° F.) temperature and reaction times up to 400 minutes (6.7 hrs) to produce glycerol, ethylene glycol, propylene glycol, and other more minor products.

U.S. Pat. No. 2,965,679 to Conradin discloses a similar process for producing glycerol and glycols from sugar alcohols using a suspended nickel on kieselguhr catalyst in an autoclave type reactor. Reaction conditions are 200°–300° C. temperature, 500–1000 atmospheric pressure and pH of 8–10, followed by filtration to remove catalyst and separation of the products.

Van Ling et al disclosed in *Journal of Applied Chemistry*, Vol. 19, pages 43–45, hydrogenation experiments using slurried catalyst in autoclave reactor on feeds of sucrose, glucose and fructose in methanol-water solution to produce glycerol. Catalyst used was $CuO$-$CeO_2$-$SiO_2$ with 0–5% $Ca(OH)_2$ addition to the feed. Reaction conditions used were 200°–250° C. temperature, 100–300 atmospheric pressure and 10–120 minutes reaction time.

U.S. Pat. No. 3,471,580 to Hellwig et al discloses that by using a single or multi-stage upflow ebullated bed catalytic reactor at 200°–550° F. temperature and 700–3500 psia hydrogen partial pressure, glycerol and glycols can be produced from saccharides. Examples of the conditions used for converting a sorbitol type feed to glycerol in a single stage reaction were about 375° F. temperature, 1700 psia hydrogen partial pressure, 1.2 liquid hourly space velocity (LHSV), and using nickel on alumina catalyst to produce roughly 50 W % glycerol and 20 W % propylene glycol, with the remainder being methanol, ethanol, isopropanol, and other products (col. 5, lines 40–53).

It is believed that none of these known processes are presently being used commercially to produce glycerol and related products on a continuous basis. Thus, further process improvements in alditol conversion for achieving continuous operations, reduced reaction conditions and increased glycerol product yields are desired, particularly using improved catalysts in fixed-bed reactors.

SUMMARY OF INVENTION

The present invention discloses an improved continuous fixed catalyst bed reaction process for converting alditols such as sorbitol, mannitol, and xylitol by hydrogenolysis to produce glycerol and polyols products. The fixed-bed type reaction zone, using an improved porous metal catalyst on inert support, operates at moderate conditions and short residence times, and provides the inherent advantages of limiting back mixing of the feed and suppressing undesired secondary reactions. This process utilizes as its feedstock solutions of alditols such as sorbitol, mannitol and xylitol, which are catalytically convertible into mainly glycerol and glycols products. The alditol feed solution is preferably an aqueous solution; however, alcohols such as methanol, ethanol, propanol, and glycols such as ethylene glycol, propylene glycol and such and mixtures thereof which have boiling points sufficiently different from glycerol to permit convenient separation by distillation may be used. A alkali promoter material, such as calcium hydroxide or sodium hydroxide, is added to the feedstream solution in concentrations to control the pH of the feedstream and reactor effluent to prevent leaching metal from the catalyst and to improve the reaction, and are usually within the range of 0.2–3 W %. The preferred feed material is 15–60 W % sorbitol in water solution for reasons of low cost and good availability.

For high conversion of alditols to continuously produce high yields of at least about 30 W % and preferably 40–60 W % glycerol products, it has been found that the reaction zone operating conditions should be maintained within the range of 420°–520° F. (216°–271° C.) temperature and 1200–2000 psig hydrogen partial pressure. The liquid hourly space velocity (LHSV) should be maintained between about 1.5 and 3.0 volumes of feed per hour per volume catalyst ($V_f$/hr/$V_c$), at which feed rate the yield of glycerol increases with the concentration of calcium hydroxide promoter between about 0.1 and 3.0 W %. For sorbitol feed, the concentration of sorbitol in aqueous solution in the feedstream should be at least about 15 W % and for best product selectivity results usually should not exceed about 60 W %, with 20–40 W % concentration usually being preferred. Also, the volume ratio of hydrogen gas/liquid in the feedstream should be at least about 1000, at standard conditions, and usually need not exceed about 5000 for achieving good contact between the liquid feed solution and catalyst. The resulting yield of glycerol from the reaction zone is 30–40 W %, with balance being glycols and other minor products.

The catalyst used in this continuous fixed-bed reaction process consists of a high activity noble metal or metals selected from Group I or VIII deposited on an inert support, preferaby containing 30–70 W % nickel, and most preferably 50–65 W % porous nickel. The catalyst support should not be dissolved by the feed solution or liquid, and may be alumina, silica or combinations thereof. Useful particle size is 4–20 mesh (0.187–0.033 inch) (U.S. Sieve Series). Good results have been obtained using an improved porous nickel catalyst material containing from 60 W % nickel on kieselguhr clay support in 6–12 mesh size and pellets 3/16 inch diameter × ⅛ inch length, and having surface area of 150–200 $M^2$/gm.

Reaction zone conditions preferred for achieving hydrogenolysis (hydrocracking) and high conversion of alditols to mainly glycerol product are 430°–480° F.

temperature and 1400–1800 psig hydrogen partial pressure. The most preferable reaction conditions are 450°–475° F. temperature, 1500–1750 psig hydrogen partial pressure, liquid space velocity within the range of 1.8 to 2.8 vol feed/hr/vol catalyst, and gas/liquid volume ratio of 1500 to 4500. The sorbitol feed concentration is preferably 15–40 W %, and the desired range of sorbitol conversion to glycerol and glycol products is 40 to 70 W % of feed.

It has been found that significant catalyst deactivation occurs due to oxidation of the nickel following operations of at least about 8 hours. However, useful catalyst activity is maintained and also product selectivity is improved by periodic regeneration of the catalyst. For regeneration, the catalyst is preferably washed with a solvent to remove deposits and then contacted by a hot reducing gas such as hydrogen passing through it at elevated temperature above the vaporization temperature of sorbitol feed and conversion products at the regeneration pressure to substantially remove the surface oxidation and residue material. Continuous operation of the process is maintained by using multiple reactors, and preferably two reactors, for which one catalyst bed is operated in parallel and the other is regenerated alternately, such as at 10–100 hour intervals and preferably at 12–50 hour intervals. Also, it has been found that the regenerated catalyst provides for improved selectivity for desired glycerol products as compared to using fresh catalyst, as undesired secondary cracking reactions are reduced by use of the regenerated catalyst.

Following catalytic reaction of the feed, the reaction zone effluent stream is pressure-reduced and passed to a recovery section comprising multiple distillation steps for removal of light products such as alcohols, water, and glycols, and for achieving increased recovery of glycerol and other desired products. Following removal of volatile materials, a portion of the heavy bottom liquid stream containing unconverted sorbitol feed is recycled to the reaction zone for further catalytic reaction and conversion to mainly glycerol product. Yield from the process following distillation is 40–50 W % glycerol based on sorbitol feed, with the balance being glycols and other minor products.

The present process for catalytic hydrogenation of alditols to produce glycerols provides the advantageous characteristics of permitting continuous operation in a downflow fixed-bed catalytic reactor configuration, and uses a very active stabilized nickel catalyst having improved selectivity following regeneration. It also uses lower hydrogen partial pressure and higher liquid hourly space velocity (LHSV) than previous known processes. All of these characteristics are combined in this invention to provide a sorbitol hydrogenolysis process which produces superior results, and is more suitable for commercial usage than the previously known processes.

DESCRIPTION OF PREFERRED EMBODIMENTS

Figure 1:
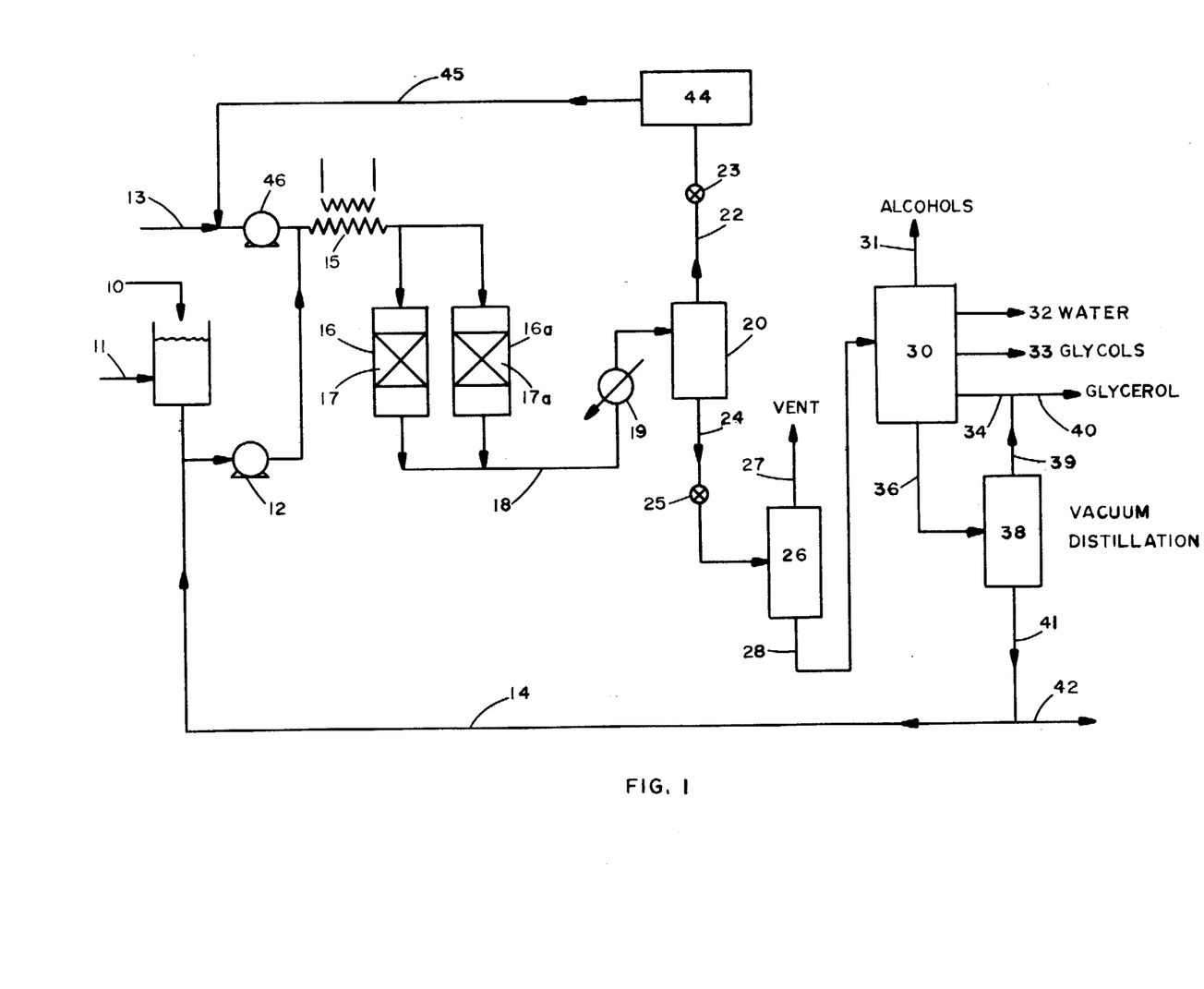
FIG. 1 is a schematic drawing showing the sorbitol hydrogenolysis process, including catalytic reaction and product distillation steps.

As shown in FIG. 1, a 20–50 W % sorbitol solution such as obtained from glucose is provided in water solution at 10. The pH is adjusted so as to prevent any substantial leaching of the nickel in the catalyst, and will usually be maintained within the range of 7–14 by addition of an alkali promotor at 11, preferably 0.5–2 W % calcium hydroxide. The resulting feedstream solution is pumped at 12 together with fresh hydrogen from 13 through preheater 15, where it is heated by any convenient means preferably with steam to above about 200° F. The feedstream is usually mixed with a recycle liquid stream 14 containing unconverted sorbitol, some $C_1$–$C_5$ alditols and some polyglycerols, and the heated mixture passed into reactor 16.

The reactor 16 contains a fixed bed of particulate catalyst 17, and the liquid feed and hydrogen gas are preferably passed downwardly through the bed in intimate contact with the catalyst. The reactor is maintained at elevated temperature and pressure conditions with the range of 430°–490° F. temperature and 1400–1900 psig hydrogen partial pressure. The sorbitol solution feed rate or liquid hourly space velocity should be at least about 1.8 and usually need not exceed about 2.8 Vf/hr/Vc for good hydrogenolysis reaction results. The hydrogen gas/liquid volume ratio should be maintained at least about 1000 for good contact between the liquid solution and catalyst, and usually need not exceed about 5000. The sorbitol is reacted and converted to at least about 30 W % glycerol along with some glycol products.

The catalyst used in reactor 16 can be a special reduced and stabilized nickel catalyst on kieselguhr support, containing 60–66 W % nickel and having 4–12 mesh particle size (0.187–0.066 inch) (U.S. Sieve Series). The catalyst becomes more active with use up to a limiting age, due to use of a "stabilized" catalyst, which is a catalyst that is covered with a mono-molecular layer of carbon dioxide to prevent spontaneous oxidation of the highly active nickel when the catalyst is exposed to the air during charging it into the reactor. In industrial practice, the catalyst is usually prereduced in situ with hydrogen to achieve maximum conversion of sorbitol to glycerols. Limiting the pretreatment step to about two hours is usually sufficient, since a catalyst with too high an initial activity may cause carbon deposition on the catalyst.

Because the catalyst becomes deactivated by oxidation during extended use and must be regenerated to maintain useful sorbitol conversion levels, a second catalyst reactor 16a is provided in parallel for alternate use. After an operation period of at least about 16 hours of catalyst use, so that the conversion of sorbitol decreases to below about 30 W %, and usually not exceeding about 200 hours, the feed is switched to alternate reactor 16a containing catalyst bed 17a. The used catalyst 17 is regenerated by first washing with water or a water-methanol solution as a solvent to remove residual liquids and deposits, and then contacting the catalyst with hydrogen at 500°–650° F. temperature and a reduced pressure, preferably atmospheric pressure for 2–10 hours duration to remove oxidation. Catalyst regeneration is preferably conducted after 16–32 hours operation by washing with 25% water–75% methanol solution for about 4 hours, followed by contacting it with flowing hydrogen at 550°–600° F. temperature and atmospheric pressure for about 8 hours.

The reactor effluent stream at 18, which has pH controlled within about 6.5 and 7.5, is cooled in heat exchanger 19 against a suitable fluid such as water, and passed to high pressure separator 20, wherein the fluid is separated into an overhead gas stream 22 and bottoms liquid stream 24. Overhead stream 22 contains mainly hydrogen and some methane and is pressure-reduced at 23 and passed to hydrogen purification unit 44. Here the gas is purified to at least about 50 V % and usually 60–80 V % hydrogen, and recycled as stream 45 through compressor 46 to the reactor 16 for reuse.

Separator bottoms stream 24 is pressure-reduced at 25 and passed to low pressure separator 26, from which overhead stream 27 is withdrawn as a gas vent stream containing hydrogen and methane. Liquid stream 28 containing mainly glycerol product is withdrawn and passed to distillation section 30 for removal of alcohols at 31, excess water at 32, and glycols such as propylene glycol and ethylene glycol at 33. A portion of glycerol product is withdrawn at 34, and the remaining glycerol is withdrawn at 36 and passed to vacuum distillation step 38. This distillation is performed at vacuum pressure of 1 to 100 mm Hg and preferably at 10–70 mm Hg pressure.

It has been found that conventional vacuum distillation procedures are slow and require relatively high differential temperatures and result in fluid tempertures above the decomposition temperature of glycerol or about 400° F., and thus allows the undesirable formation of poly glycerides in the product. Accordingly, to provide such distillation of product more rapidly and at minimum temperature, preferably not exceeding about 400° F. to limit undesired side reactions, thin film type evaporation is preferably provided for distillation step 38 such as falling film-type or wiped film-type evaporator.

The remaining glycerol product having 40–60 W % concentration is withdrawn overhead at 39 and combined with stream 34 to provide glycerol product stream 40. A heavy liquid stream containing unconverted sorbitol from distillation step 38 is withdrawn at 41, and is recycled to reactor 16 for further conversion to produce the desired glycerol product. A purge stream containing heavy unconverted material which is not readily converted at the sorbitol conversion conditions can be withdrawn at 42 for discard or further processing as desired.

Figure 2:
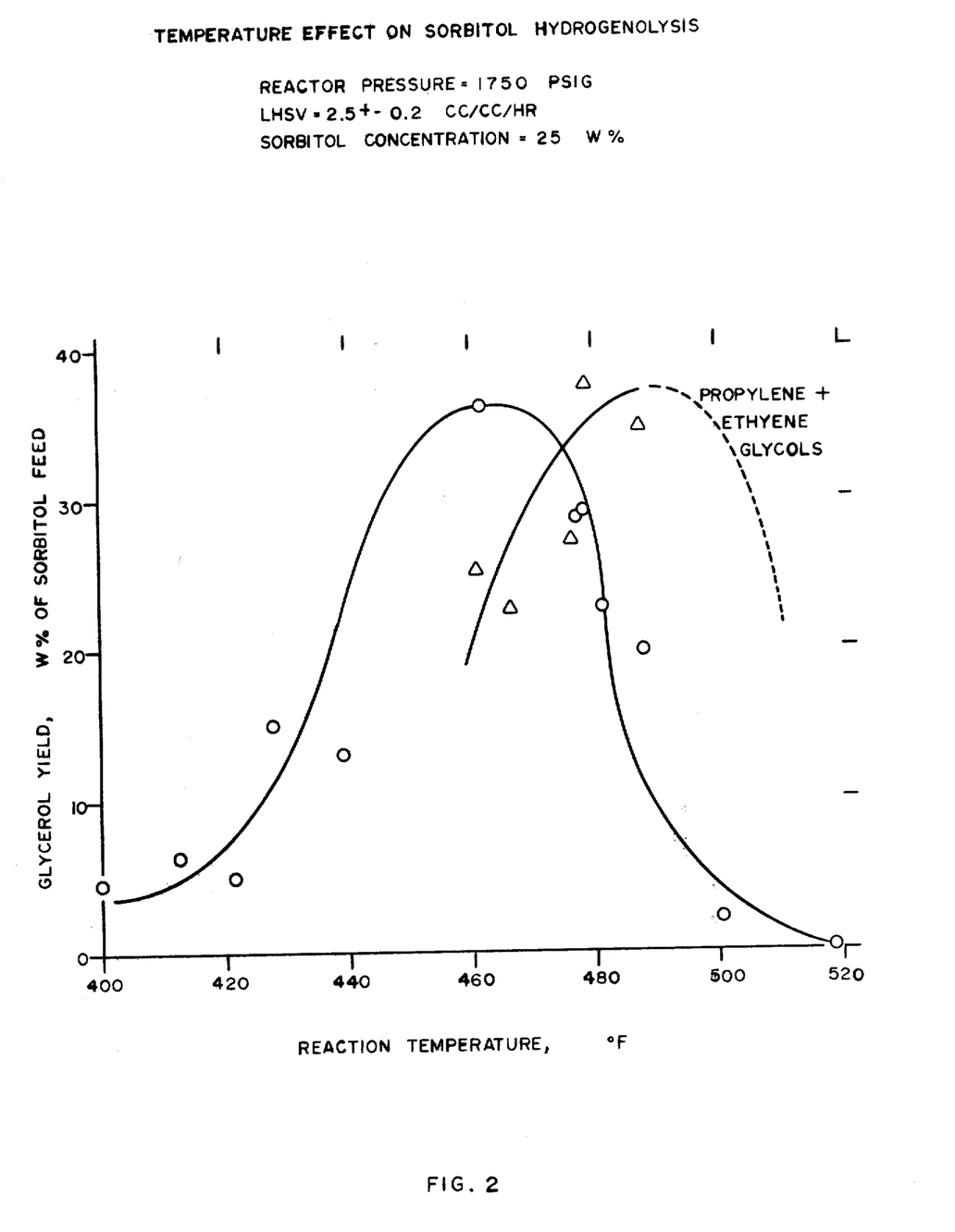
FIGS. 2 to 5 are graphs showing sorbitol hydrogenolysis results under various reaction conditions.
Figure 3:
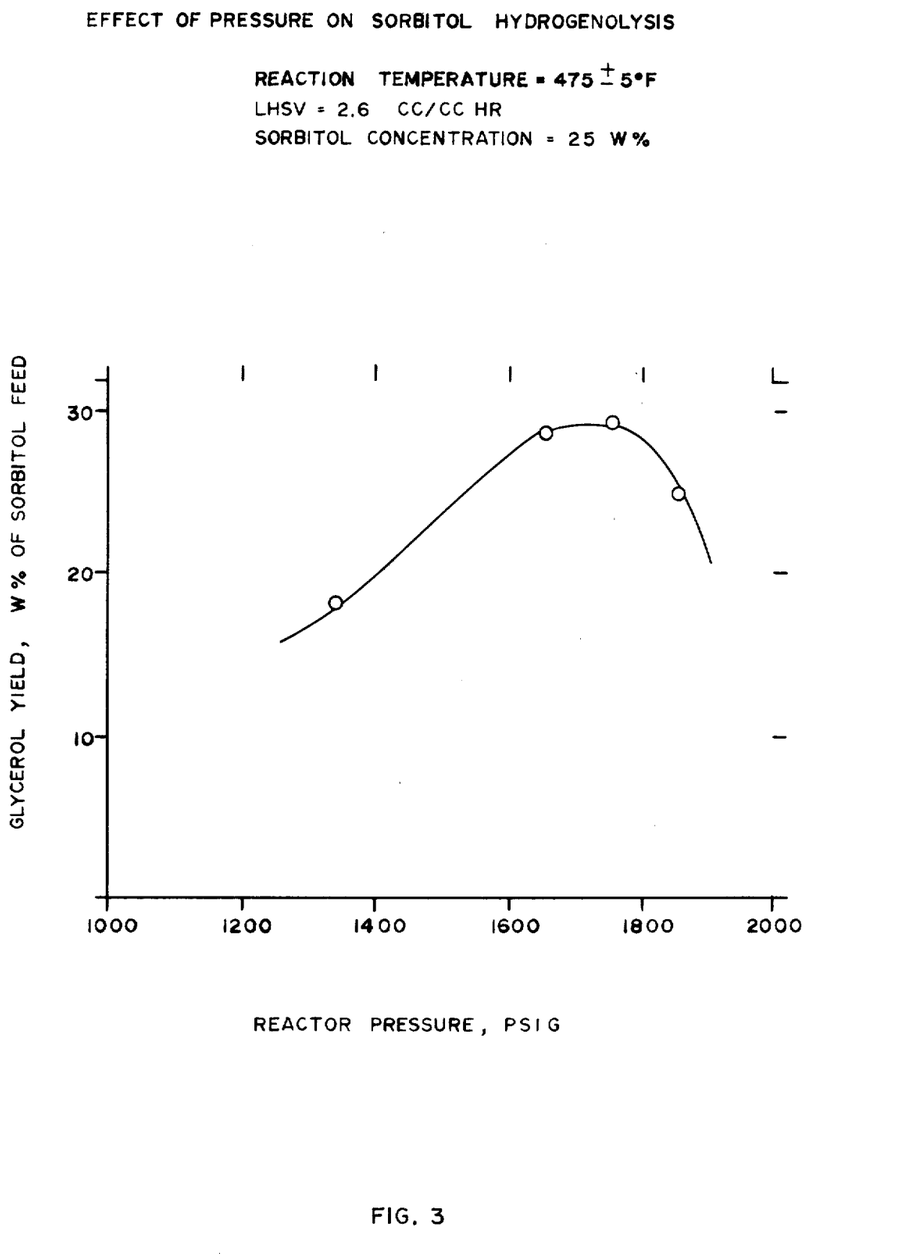
Figure 4:
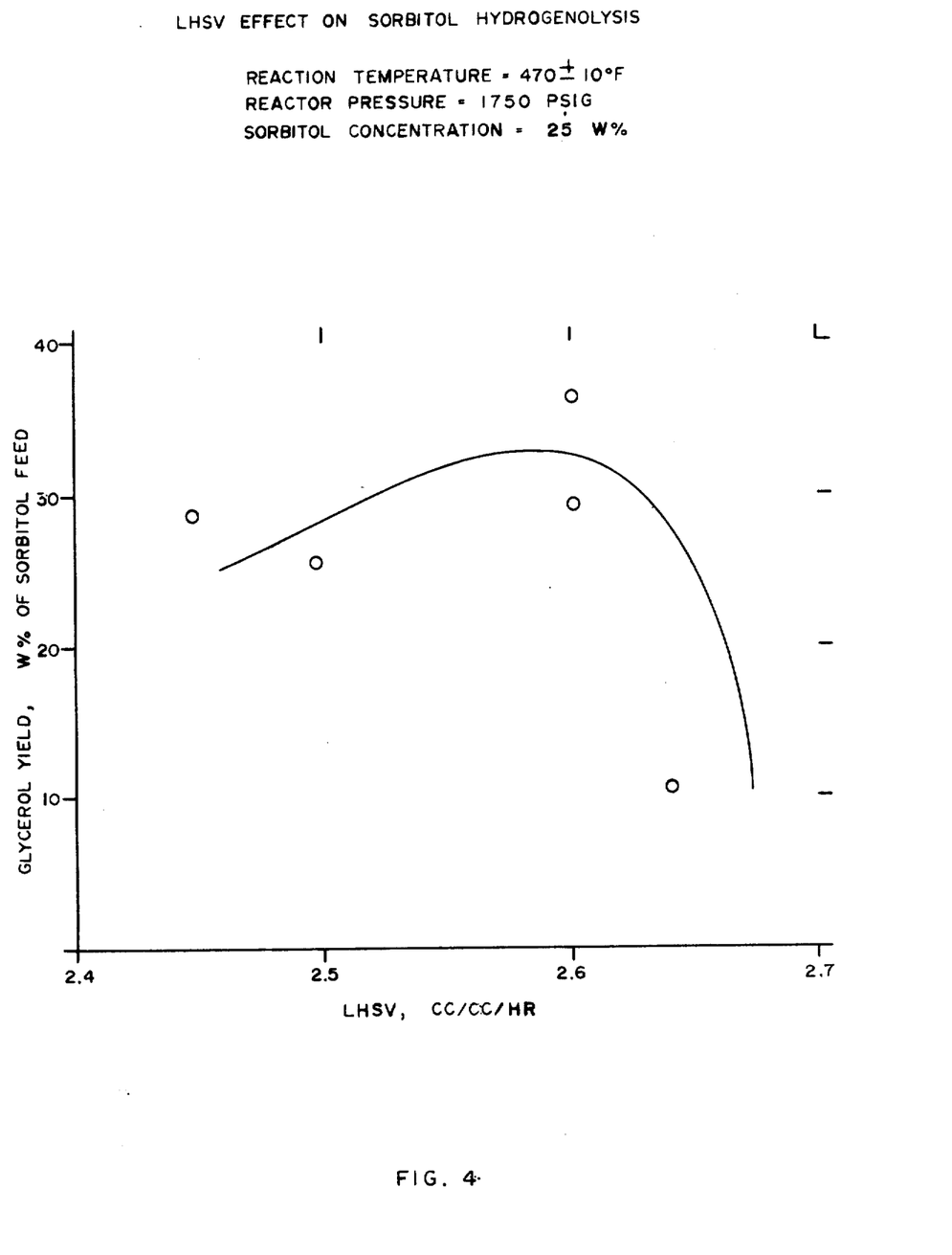

Typical effects on sorbitol conversion of the parameters of reactor temperature, hydrogen partial pressure, and liquid hourly space velocity are shown in FIG. 2–4. It is noted from FIGS. 2 and 3 that a significant reduction in percent sorbitol conversion to glycerol occurs outside the desired range of about 430°–490° F. temperature and about 1400–1900 psig hydrogen partial pressures. As shown in FIG. 4, percent conversion is reduced for liquid hourly space velocities less than about 2.5 and greater than 2.65 V/hr/Vc.

This invention is further illustrated by the following examples, which should not be construed as limiting the scope of the invention.

EXAMPLE 1

Sorbitol 70% USP grade solution, was diluted by adding distillated water to provide 25 W % and 40 W % sorbitol concentration to make feedstock samples. Industrial grade hydrogen (99.5%) was used from a 3000 psig plant distribution system. Calcium hydroxide, Ca(OH)$_2$, was added to the sorbitol solutions in 0.1 and 1.0 W % concentrations as a reacton promotor material and to adjust the pH to about 11–13.

The prepared feedstocks and hydrogen were heated to 250° F. and introduced into a fixed-bed reactor system for sorbitol hydrogenolysis. The process steps used were very similar to the schematic diagram shown in FIG. 1. The downflow reactor was fabricated from Schedule 160 stainless steel pipe, 0.464 inch inside diameter by 12 inches long, providing a volume of 33 cc. The bottom portion of the reactor was filled with 20 cc catalyst comprising 60 W % porous nickel on kieselguhr support and having 8–12 mesh particle size (U.S. Sieve Series) obtained from United Catalyst Company. The top portion of the reactor contained 8–12 mesh tabular alumina and served as a feed preheating and flow distribution section. The reactor was equipped with a three-point thermocouple to monitor the temperature at the top, middle and bottom of the catalyst bed.

Sorbitol hydrogenolysis (hydrocracking) operations were conducted using a range of reactor operating conditions selected as follows:

Reaction Temperature, °F.: 400–520
Hydrogen Partial Pressure, psig: 1350–1850
Liquid Space Velocity, cc/hr/cc catalyst: 1.6–3.0
H$_2$ Gas/Liquid Ratio: 1000–5000

A gas chromatograph equipped with a hydrogen-flame ionization detector and an integrator was used for sample analysis. An "alcohol" analysis was carried out on all the samples, but only selected samples were analyzed for aldoses and alditols. Detailed analytical procedure involved using a 80/100 mesh Porapak P column 2 mm dia. ×4 ft. long and made of stainless steel for alcohol, glycol, and polyol analysis. One microliter of sample was injected into the column. The gas chromatograph conditions were set at: initial column temperature, 150° C.; hold-up time at 150° C., 4 minutes; temperature increase rate, 8° C./min; final temperature, 230° C.; helium flow rate; 30 cc/min; injector and interface temperature, 300° C.; head pressure of gases; air-50 psig, helium-100 psig, hydrogen-20 psig.

Several series of runs were conducted to study the effects of Ca(OH)$_2$ promoter concentration, reaction temperature, hydrogen partial pressure, liquid hourly space velocity, and sorbitol feed concentration on product yields. It was observed that 1% Ca(OH)$_2$ solution gave generally better glycerol yields than 0.1% Ca(OH)$_2$ solution. All subsequent data were obtained with a 1% Ca(OH)$_2$ solution. Apparently, glycerol is quite susceptible to hydrogenation and hydrocracking and is converted to glycols, as noted in FIG. 2 showing effect of reaction temperature upon glycerol yields. FIG. 3 shows the effect of hydrogen partial pressure on glycerol yield, with optimum pressure being about 1600–1800 psig. The optimum space velocity shown by FIG. 4 is about 2.55–2.6 cc/hr/cc of catalyst.

Regarding sorbitol concentration in the feed, data showed that the 25 W% sorbitol solution gives a better glycerol yield than the 40 W % solution at the same reaction conditions. For a 1% Ca(OH)$_2$ promotor and 25 W % sorbitol solution, the optimum operating conditions were found at about 460° F., 1750 psig, and 2.6 cc/hr/cc of catalyst, at which condition the conversion of sorbitol to glycerol was 36.4 W %.

Figure 5:
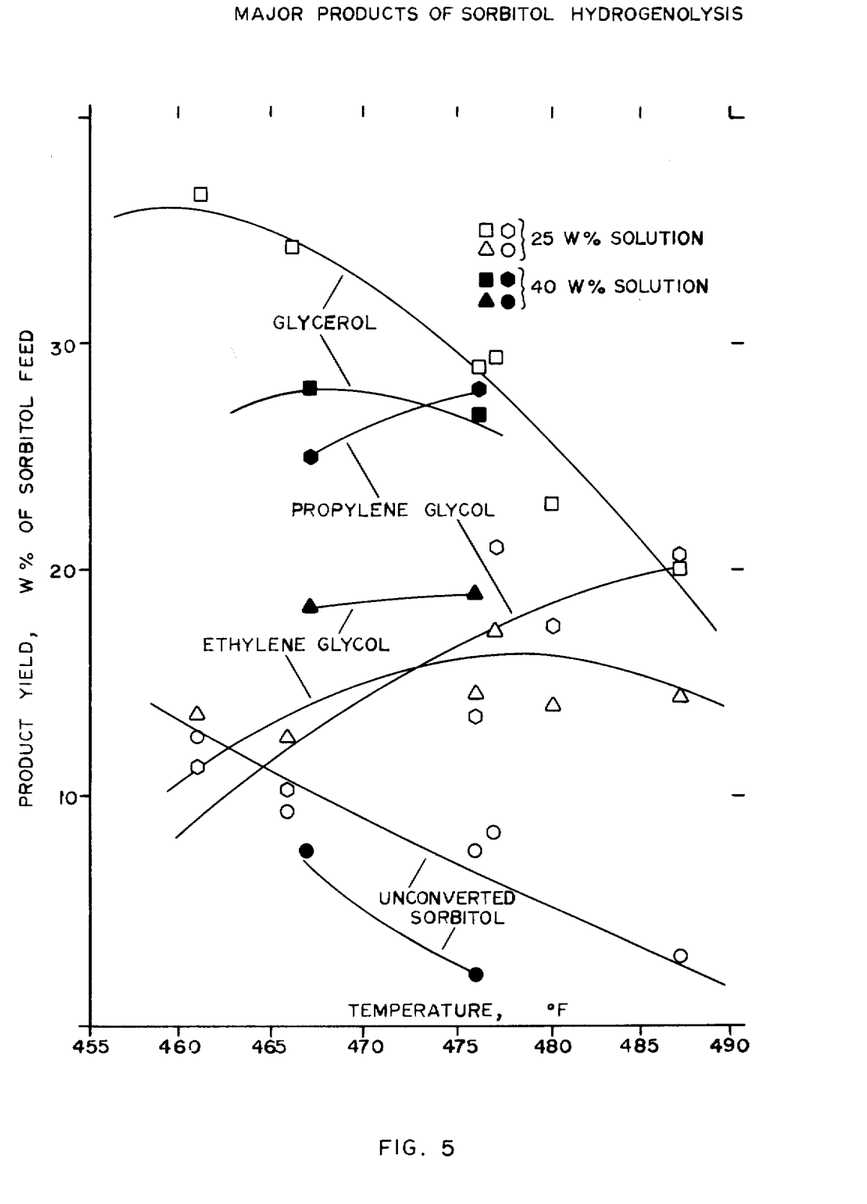

FIG. 5 shows a detailed analysis of the products obtained in the runs at reaction temperatures between 460° F. and 490° F. with both 25 W % and 40 W % sorbitol feed solutions. The data clearly illustrate the concentration trends of each compound formed in the reaction, and that glycerol yield is increased for lower sorbitol concentrations in the feedstream and by lower reaction zone temperatures. The major products were identified as glycerol, propylene glycol and ethylene glycol. The minor products were butanediols, diethylene glycol, methanol, ethanol, propanol, mannitol, xylitol and erythritol. The hydrogenolysis of sorbitol is characterized by the cleavage positions of the carbon bonds and it was found that the cracking probability follows the order of $C_3-C_3 > C_2-C_4 > C_1-C_5$.

EXAMPLE 2

Figure 6:
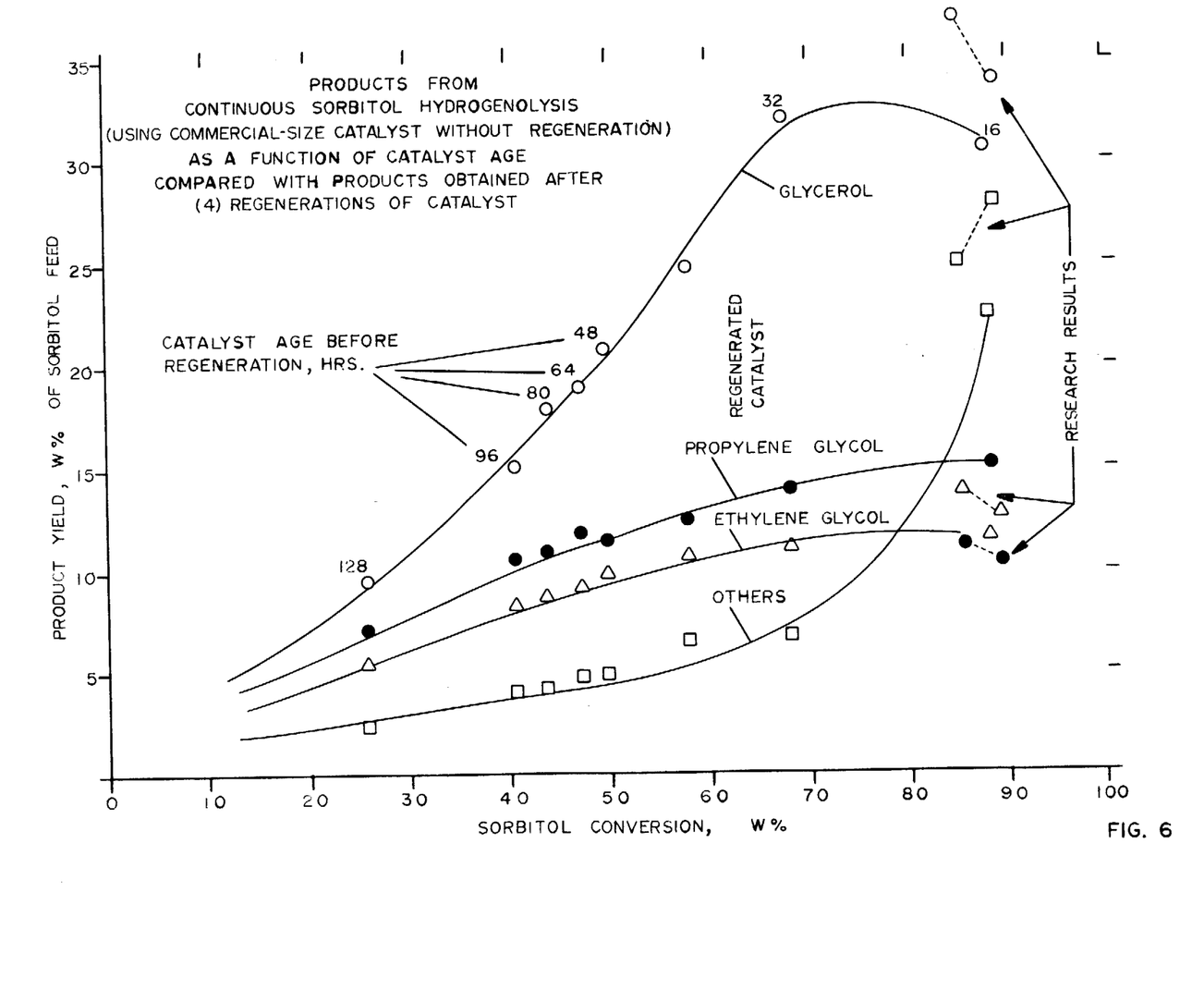
FIG. 6 is a graph showing the benefits of catalyst regeneration in maintaining product yield.

Additional operations for sorbitol hydrogenolysis were conducted in a reactor 1.0 inch inside diameter × 15 inches high, using pelletized catalyst ⅛ inch diameter × 3/16 inch long, composed of 60% porous nickel on kieselguhr support. It was found that activity of the 60% porous nickel on kieselguhr catalyst declined after about 20 hours operation, and continued to decline after about 130 hours use, as shown in FIG. 6. To restore catalyst activity, a catalyst regeneration procedure was developed, wherein the used catalyst was washed with a solution containing 25 W % water and 75 W % methanol, followed by contacting the catalyst with hydrogen at 575° F. at atmospheric pressure and hydrogen flow rate of 0.125 ft³/min for 4 hours. After regeneration, catalyst activity was improved sufficiently to achieve about 60 W % sorbitol conversion and about 25 W % yield of glycerol. Results using both fresh and regenerated catalyst are shown in FIG. 6.

It is seen that fresh catalyst activity for sorbitol conversion declined appreciably following about 32 hours (two 16-hour periods) of use without regeneration, and glycerol yield declined to about 10% of sorbitol feed after eight 16-hour periods (128 hours) of use. Following catalyst regeneration, sorbitol conversion increased to about 60 W % and the glycerol yield increased to about 25 W % of sorbitol feed. Thus, it is seen that regeneration of the catalyst should usually occur between about two and four 16-hour periods of use, or after about 32–64 hours of use, and may occur sooner, if desired. The catalyst regeneration procedure desirably maintains sorbitol conversion between about 50 and 70 W % of feed, and with recycle of unconverted sorbitol permits producing 40–50 W % yield of glycerol, based on sorbitol converted. Also, it is noted that the selectivity for glycerol product is improved when using regenerated catalyst as compared to fresh catalyst after about 50 hours operation, because the production of other cracking and hydrogenation products is greatly reduced.

Although this invention has been described in terms of the accompanying drawings and preferred embodiment, it is recognized that many modifications of this invention can be made without departing from the spirit and scope thereof, which is defined solely by the following claims.

We claim:

1. A process for catalytic hydrogenolysis of an alditol solution to produce glycerol and polyols, comprising the steps of:

(a) providing a feedstream solution containing at least about 10 W % alditol and adding an alkaline promoter material to the feestream sufficient to provide a pH within the range of 7–14;

(b) preheating the feed solution and hydrogen gas to at least about 200° F. temperature, and introducing the heated feedstream mixture into a fixed bed reaction zone containing a particulate high activity stabilized nickel catalyst containing 50–65 W % porous nickel on silica support and having 4–20 mesh (0.187–0.033 inch) particle size (U.S. Sieve Series), said catalyst being regenerated after 20–60 hours use by washing it with a water-methanol solution and then contacting said catalyst with flowing hydrogen at 550°–600° F. temperature and at reduced pressure for 2–8 hours to provide improved selectivity for a glycerol product;

(c) maintaining the reaction zone conditions within the range of 420°–500° F. temperature, 1200–2000 psig hydrogen partial pressure, 1.5–3.0 liquid hourly space velocity (LHSV), and catalyst age exceeding about 8 hours for achieving at least about 30 W % conversion of the alditol to glycerol and glycol products;

(d) withdrawing from the reaction zone a stream containing glycerol and glycols and phase separating said stream into a gaseous portion and a liquid portion;

(e) distilling said liquid portion to remove alcohols, water and glycols to produce higher purity glycerol product, and a heavy bottoms liquid stream containing alditols; and (f) recycling at least a portion of said bottoms stream to the reaction zone for further catalyst conversion of alditols to mainly glycerol product.

2. The process of claim 1, wherein the feedstream contains 20–60 W % sorbitol in aqueous solution, the reaction zone conditions are maintained within the range of 430°–480° F. temperature, 1400–1900 psig hydrogen partial pressure, 1.8–2.8 liquid hourly space velocity, said nickel catalyst age being maintained at 10–200 hours by washing said catalyst with a water-methanol solution and then contacting said catalyst with flowing hydrogen at 550°–600° F. temperature and at reduced pressure for 2–8 hours, and wherein the sorbitol feed solution is converted about 30–70 W % to yield mainly glycerol product with the remainder being glycols and other products.

3. The process of claim 2, wheren the promotor added to the feedstream in (a) is calcium hydroxide solution and pH of the reactor effluent is between about 6.5 and 7.5.

4. The process of claim 2, wherein multiple catalytic reaction zones are provided in parallel so as to permit continuous operation using one reaction zone while regenerating the catalyst in an other zone whenever the alditol conversion therein declines to below about 40 W %.

5. The process of claim 2, wherein the catalyst comprises 50–65 W % porous nickel on silica support and has 4–20 mesh (0.187–0.033 inch) particle size (U.S. Sieve Series).

6. The process of claim 2, wherein further glycerol product separation is achieved by vacuum distillation of the feed liquid portion at 1–100 mm of mercury pressure to remove unconverted alditol and produce 40–90 W % purity glycerol product.

7. The process of claim 6, wherein the final distillation step utilizes thin film type evaporation to provide a distillation temperature not exceeding about 400° F. to minimize undesired side reactions therein.

8. The process of claim 2, wherein the catalyst age is controlled by regeneration following at least 10 hours use, by washing said used catalyst with a water-methanol solution to remove deposits and then contacting the catalyst with a reducing gas at temperature above the reaction temperature and at reduced pressure for at least about 2 hours, then returning the catalyst to use.

9. The process of claim 1, wherein the volume ratio of hydrogen gas to feed liquid at standard conditions is within the range of 1000 and 5000.

10. The process of claim 2, wherein the feedstream contains 20-45 W % sorbitol, the reaction zone conditions are maintained within the range of 450°-475° F. temperature, 1400-1900 psig hydrogen partial pressure, 2.0-2.7 liquid hourly space velocity, catalyst age is maintained at 10-200 hours by periodic regeneration, and wherein the sorbitol feed solution is converted about 30-70 W % to yield mainly glycerol product with the remainder being glycols and other products and the glycerol yield increases as sorbitol concentration in the feed and reaction temperature are decreased.

11. A process for catalytically converting sorbitol solution to produce mainly glycerol product, comprising the steps of:
(a) providing a feedstream containing 20-60 W % sorbitol in aqueous solution;
(b) adding calcium hydroxide promoter to the feedstream sufficient to provide a pH within the range of 7-14;
(c) preheating the feed solution together with hydrogen gas to at least about 200° F., and introducing the heated feedstream mixture into a fixed-bed reaction zone containing a particulate high activity stabilized nickel catalyst containing 50-65 W % porous nickel on silica support and having 4-20 mesh (0.187-0.33 inch) particle size (U.S. Sieve Series), said catalyst being regenerated after 20-60 hours use by washing it with a water-methanol solution and then contacting said catalyst with flowing hydrogen at 550°-600° F. temperature and at reduced pressure for 2-8 hours to provide improved selectivity for a glycerol product;
(d) maintaining the reaction zone conditions within the range of 430°-480° F. temperature, 1400-1900 psig hydrogen partial pressure, 1.8-2.8 liquid hourly space velocity (LHSV) and catalyst age of 10-200 hours for achieving 30-70 W % conversion of the sorbitol to yield mainly glycerol with the remainder being alcohols and glycols;
(e) withdrawing from the reaction zone a stream containing glycerol and glycol products and phase separating said stream into a gaseous portion and a liquid portion;
(f) reducing pressure of said liquid portion and passing it to a vacuum distillation step maintained at 10-80 mm Hg pressure to remove water vapor and produce 40-90 W % purity glycerol product and a heavy bottoms liquid stream containing unconverted sorbitol and other alditols; and
(g) recycling at least a portion of said bottoms stream to the reaction zone for further catalytic conversion of sorbitol to mainly glycerol product.

12. A process for catalytic hydrogenolysis of an alditol solution to produce glycerol, comprising the steps of:
(a) providing a feedstream containing at least about 10 W % alditol in water solution and adding an alkaline promotor material to the feedstream to provide a pH within a range sufficient to prevent leaching of the catalyst metal;
(b) preheating the feed solution together with hydrogen gas to at least about 200° F. temperature, and introducing the heated feedstream mixture into a reaction zone with a particulate high activity stabilized nickel catalyst containing 50-65 W % porous nickel on silica support and having 4-20 mesh (0.187-0.033 inch) particle size (U.S. Sieve Series), said catalyst being regenerated after 20-60 hours use by washing it with a water-methanol solution and then contacting said catalyst with flowing hydrogen at 550°-600° F. temperature and at reduced pressure for 2-8 hours to provide improved selectivity for a glycerol product;
(c) maintaining the reaction zone conditions within the range of 430°-490° F. temperature, 1200-2000 psig hydrogen partial pressure, 1.5-3.0 liquid hourly space velocity (LHSV), for achieving at least about 30 W % conversion of the alditol to glycerol and glycol products;
(d) withdrawing from the reaction zone a stream containing glycerol and glycols and phase separating said stream into a gaseous portion and a liquid portion;
(e) distilling said liquid portion to remove alcohols, water and glycols to produce high purity glycerol stream at 1-100 mm Hg pressure using thin film evaporation at temperature not exceeding about 400° F. to produce glycerol product and a heavy bottoms liquid stream containing alditols; and
(f) recycling at least a portion of said vacuum distillation bottoms stream to the reaction zone for further catalytic conversion of alditols to mainly glycerol product.

* * * * *